(12) United States Patent
Shkolnik

(10) Patent No.: US 7,179,345 B2
(45) Date of Patent: *Feb. 20, 2007

(54) INFLATABLE BALLOON CATHETER SEAL AND METHOD

(75) Inventor: Boris Shkolnik, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/193,887

(22) Filed: Jul. 29, 2005

(65) Prior Publication Data

US 2005/0267409 A1    Dec. 1, 2005

Related U.S. Application Data

(62) Division of application No. 10/407,356, filed on Apr. 4, 2003, now Pat. No. 6,982,024, which is a division of application No. 09/487,128, filed on Jan. 19, 2000, now Pat. No. 6,723,113.

(51) Int. Cl.
  *B32B 31/00*  (2006.01)
  *A61M 25/00* (2006.01)
  *A61M 25/10* (2006.01)

(52) U.S. Cl. .................. 156/293; 156/84; 156/294; 604/93.01; 604/95.01; 604/103; 604/103.09

(58) Field of Classification Search ............... None
See application file for complete search history.

(56) References Cited

U.S. PATENT DOCUMENTS

| | | | |
|---|---|---|---|
| 3,866,599 A | 2/1975 | Johnson | |
| 4,147,169 A | 4/1979 | Taylor | |
| 4,406,653 A | 9/1983 | Nunez | |
| 4,413,989 A * | 11/1983 | Schjeldahl et al. | 604/103.13 |
| 4,702,252 A | 10/1987 | Brooks et al. | |
| 4,744,366 A | 5/1988 | Jang | |
| 4,811,737 A | 3/1989 | Rydell | |
| 4,819,751 A | 4/1989 | Shimada et al. | |
| 4,850,348 A | 7/1989 | Pell et al. | |
| 4,938,220 A | 7/1990 | Mueller, Jr. | |
| 4,943,278 A | 7/1990 | Euteneuer et al. | |
| 4,981,478 A | 1/1991 | Evard et al. | |
| 4,994,072 A | 2/1991 | Bhate et al. | |
| 5,035,705 A | 7/1991 | Burns | |
| 5,049,130 A | 9/1991 | Powell | |
| 5,135,486 A | 8/1992 | Eberle et al. | |
| 5,176,661 A | 1/1993 | Evard et al. | |
| 5,176,698 A | 1/1993 | Burns et al. | |
| 5,195,969 A | 3/1993 | Wang et al. | |
| 5,195,972 A | 3/1993 | Inoue | |

(Continued)

FOREIGN PATENT DOCUMENTS

EP    0 366 478    5/1990

(Continued)

*Primary Examiner*—Justin R. Fischer

(57) ABSTRACT

An improved balloon catheter seal which may be used for attaching an inflatable balloon to a catheter body, especially when the balloon and catheter body are formed from dissimilar materials. The seal is formed by applying a layer of adhesive material between the inflatable balloon and the catheter body, and crimping a retaining ring over each seal junction. The invention is especially useful when joining a compliant balloon made from silicone to a catheter body made from polyurethane.

8 Claims, 2 Drawing Sheets

U.S. PATENT DOCUMENTS

| | | |
|---|---|---|
| 5,226,889 A | 7/1993 | Sheiban |
| 5,256,145 A | 10/1993 | Atkinson et al. |
| 5,267,959 A | 12/1993 | Forman |
| 5,429,605 A | 7/1995 | Bernd et al. |
| 5,514,073 A | 5/1996 | Miyata et al. |
| 5,534,007 A | 7/1996 | St. Germain et al. |
| 5,637,365 A | 6/1997 | Carlblom |
| 5,643,209 A | 7/1997 | Fugoso et al. |
| 5,700,243 A | 12/1997 | Narciso, Jr. |
| 5,711,754 A | 1/1998 | Miyata et al. |
| 5,728,063 A | 3/1998 | Preissman et al. |
| 5,728,065 A | 3/1998 | Follmer et al. |
| 5,749,849 A | 5/1998 | Engelson |
| 5,759,173 A | 6/1998 | Preissman et al. |
| 5,850,348 A | 12/1998 | Berman |
| 5,876,376 A | 3/1999 | Schwab et al. |
| 6,068,634 A | 5/2000 | Lorentzen Cornelius et al. |
| 6,102,891 A | 8/2000 | Maria van Erp |
| 6,139,525 A * | 10/2000 | Davis-Lemessy et al. .. 604/103 |
| 6,231,588 B1 | 5/2001 | Zadno-Azizi |
| 6,254,570 B1 | 7/2001 | Rutner et al. |
| 6,270,504 B1 | 8/2001 | Lorentzen Cornelius et al. |
| 6,375,637 B1 | 4/2002 | Campbell et al. |
| 6,517,548 B2 | 2/2003 | Lorentzen Cornelius et al. |

FOREIGN PATENT DOCUMENTS

| | | |
|---|---|---|
| NL | 1008178 | 2/1998 |
| WO | WO 00/64524 | 11/2000 |
| WO | WO 00/164524 | 11/2000 |
| WO | WO 80/01353 | 4/2003 |

* cited by examiner

INFLATABLE BALLOON CATHETER SEAL AND METHOD

CROSS-REFERENCE TO RELATED APPLICATION;

This patent application is a divisional patent application of U.S. patent application Ser. No. 10/407,356, filed on Apr. 4, 2003, now U.S. Pat. No. 6,982,024, entitled, "Inflatable Balloon Catheter Seal And Method," which is a divisional patent application of U.S. patent application Ser. No. 09/487,128, filed on Jan. 19, 2000, now U.S. Pat. No. 6,723,113, entitled, "Inflatable Balloon Catheter Seal And Method."

BACKGROUND OF THE INVENTION

1. Field of the Invention

This invention relates to vascular balloon catheters which may be used for percutaneous transluminal angioplasty procedures, or alternatively may be used to position and expand a reinforcing stent within a blood vessel. In particular, this invention is especially adapted to treatment of small diameter blood vessels within the brain and may, for example, be used to temporarily occlude a blood vessel to evaluate the results of the occlusion prior to placing a permanent occlusion device within the vessel.

2. Description of the Prior Art

Medical catheters exist for a wide variety of purposes, including diagnostic procedures and interventional therapy, such as drug delivery, drainage, and perfusion. Catheters for each of these purposes may be introduced to numerous target sites within a patient's body by guiding the catheter through the vascular system. A wide variety of specific catheter designs have been proposed for such different uses.

Of particular interest to the present invention, small diameter tubular access catheters are presently being used for diagnostic and interventional therapy techniques for vessels within the brain, such as the imaging and treatment of aneurysms, tumors, arteriovenous malformations, and fistulas. Such techniques place a number of requirements on the catheters that are to be employed. The primary requirement is size. The blood vessels in the brain are frequently as small as several millimeters, or less, requiring that catheters have an outside diameter as small as one French (0.33 millimeters). In addition to small size, the brain vasculature is highly tortuous, requiring that catheters used in vessels of the brain be very flexible, particularly at their distal ends, to pass through the regions of tortuosity. Additionally, the blood vessels of the brain are relatively fragile, so it is desirable that the catheters have a soft, non-traumatic exterior to prevent injury.

Balloon catheters are typically formed by bonding an inflatable balloon to a catheter body. Typically, the inflatable balloon is stiff, or non-compliant, and must be properly sized to avoid damaging the fragile blood vessels. The inflatable balloon section is usually thermally or chemically similar to the catheter body, allowing the bond to be formed using adhesive or thermal means. When the balloon is inflated, the construction of the non-compliant balloon causes most of the force to be applied to the inflatable section of the balloon rather than on the bond between the balloon and catheter body. On the other hand, balloons made of compliant materials reduce the need for precise sizing of the balloon. However, due to the chemical differences, adhesives do not form strong bonds between compliant materials, like silicone, and typical catheter-body materials, like polyurethane. When a compliant balloon is inflated, the force on the bond between the compliant balloon and catheter body causes the balloon to peel away from the catheter body. Eventually, the bond fails.

U.S. Pat. No. 4,850,348 to Pell et al., discloses an endotracheal tube with a cuff secured to the outer surface of the tube. The cuff is inflated by means of a pilot balloon connected to the cuff by an external tube and internal passage in the wall of the tube. The distal end of the cuff has an annular end that is secured in contact with the tube and faces in the direction of the proximal end of the tube. Thus, the annular end and distal radiopaque band are located interior to the cuff body.

U.S. Pat. No. 5,876,376 to Schwab et al., discloses a catheter balloon bonding stopper in which the stopper is used to prevent adhesive from wicking between the catheter body and the balloon tail into the balloon. U.S. Pat. No. 5,643,209 to Fugoso et al., discloses an adhesive bond between the inner surface of the distal tail of the balloon and the outer surface of the guidewire shaft. The adhesive bond continues as a filler beyond the balloon distal tip and gradually tapers distally to the same diameter as the outer diameter of the guidewire shaft step down portion.

U.S. Pat. No. 5,700,243 to Narcisco, Jr., discloses radiopaque bands used to crimp a balloon on a catheter shaft. U.S. Pat. No. 3,866,599 to Johnson, discloses clamping rings employed to attach an expandable sleeve to the body of a catheter.

SUMMARY OF THE INVENTION

In accordance with the present invention, there is provided a balloon catheter having a balloon and a catheter body formed of dissimilar polymeric materials. The balloon catheter includes a catheter body that includes an outer tubular member and an inner tubular member that is coaxial with and runs longitudinally through the outer tubular member and extends distally beyond the distal end of the outer tubular member, and an inflatable balloon. The outer and inner tubular members are formed from a first polymeric material. The inflatable balloon is formed from a second polymeric material, which differs from the first polymeric material. The inflatable balloon is attached at the proximal end by a first layer of adhesive material interposed between the inner surface of the proximal portion of the balloon and the distal end of the outer tubular member to bond the inner surface of the proximal portion of the balloon to the distal end of the outer tubular member. This bond is reinforced by a first retaining ring positioned over and crimped tightly around the proximal portion of the balloon. Similarly, the inflatable balloon is attached at the distal end by a second layer of adhesive material interposed between the inner surface of the distal portion of the balloon and the distal end of the inner tubular member. This bond is reinforced by a second retaining ring positioned over and crimped tightly around the distal portion of the balloon. In addition, the balloon catheter includes a coupling member, having a lumen extending therethrough, mounted on the proximal end of the outer tubular member and the lumen of the coupling member communicating with the lumen between the outer tubular member and the inner tubular member so that fluid may be injected into the lumen of the coupling member to inflate the balloon.

In accordance with another aspect of the present invention, the first polymeric material is formed of polyurethane, the second polymeric material is formed of silicone, and the first and second layers of adhesive materials are formed of silicone.

In accordance with another aspect of the present invention, there is provided a balloon catheter having a balloon and a catheter body. The balloon catheter includes a catheter body that includes an outer tubular member and an inner tubular member that is coaxial with and runs longitudinally through the outer tubular member and extends distally beyond the distal end of the outer tubular member, and an inflatable balloon. The inflatable balloon is attached at the proximal end by a first layer of adhesive material interposed between the inner surface of the proximal portion of the balloon and the distal end of the outer tubular member to bond the inner surface of the proximal portion of the balloon to the distal end of the outer tubular member. This bond is reinforced by a first retaining ring positioned over and crimped tightly around the proximal portion of the balloon. Similarly, the inflatable balloon is attached at the distal end by a second layer of adhesive material interposed between the inner surface of the distal portion of the balloon and the distal end of the inner tubular member. This bond is reinforced by a second retaining ring positioned over and crimped tightly around the distal portion of the balloon. In addition, the balloon catheter includes a coupling member, having a lumen extending therethrough, mounted on the proximal end of the outer tubular member and the lumen of the coupling member communicating with the lumen between the outer tubular member and the inner tubular member so that fluid may be injected into the lumen of the coupling member to inflate the balloon.

In accordance with another aspect of the present invention, the first and second retaining rings are formed of a radiopaque material and serve as radiopaque marker bands for positioning the proximal and distal ends of the balloon, respectively. Preferably, the radiopaque marker bands are formed of a biocompatible metallic substance such as gold.

In accordance with yet another aspect of the present invention, the balloon catheter may include proximal and distal retaining ring sleeves. The proximal retaining ring sleeve overlaps the proximal end of the first retaining ring by at least half of the length of the first retaining ring and is heat fused to the outer tubular member and the first retaining ring. The distal retaining ring sleeve is positioned distally adjacent to the second retaining ring and is heat fused to the inner tubular member. The proximal and distal retaining ring sleeves serve to prevent the first and second retaining rings, respectively, from moving along the length of the outer or inner tubular member. Preferably, the proximal retaining ring sleeve is formed of nylon and the distal retaining ring sleeve is formed of polyurethane.

In accordance with still another aspect of the present invention, there is presented a method of manufacturing a balloon catheter that includes an outer tubular member, an inner tubular member, and an inflatable balloon. The method includes the steps of applying a first layer of adhesive material to the distal end of the outer tubular member, inserting the proximal portion of the balloon over the section of the outer tubular member covered by the first layer of adhesive material such that the balloon and the outer tubular member are coaxially oriented, positioning a first retaining ring over the proximal portion of the balloon, crimping a first retaining ring onto the proximal portion of the balloon, inserting the inner tubular member inside the balloon, positioning a second retaining ring over the balloon, applying a second layer of adhesive material onto the distal end of the inner tubular member at a location beneath the distal portion of the balloon, and crimping the second retaining ring onto the distal portion of the balloon.

In accordance with still another aspect of the present invention, there is presented a method of manufacturing a balloon catheter that includes an outer tubular member, an inner tubular member, and an inflatable balloon is presented. The method includes the steps of applying a first layer of adhesive material to the distal end of the outer tubular member, inserting the proximal portion of the balloon over a portion of the outer tubular member covered by the first layer of adhesive material such that the balloon and outer tubular member are coaxially oriented, positioning the first retaining ring over the proximal portion of the balloon, crimping the first retaining ring onto the proximal portion of the balloon, positioning a proximal retaining ring sleeve over at least a half of the first retaining ring and extending over a proximal portion of the first retaining ring, heat fusing the proximal retaining ring sleeve to the outer tubular member and the first retaining ring, inserting the inner tubular member inside the balloon, positioning the second retaining ring over the balloon, applying a second layer of adhesive material onto the distal end of the inner tubular member at a location beneath the distal portion of the balloon, crimping the second retaining ring onto the distal portion of the balloon, positioning a distal retaining ring sleeve distally adjacent to the second retaining ring, and heat fusing the distal retaining ring sleeve to the inner tubular member.

In accordance with still another aspect of the present invention, the method of manufacturing the balloon catheter further includes the step of tapering at least a portion of the distal end of the outer tubular member prior to applying the first layer of adhesive material over the portion of the distal end that is tapered.

DESCRIPTION OF A PREFERRED EMBODIMENT

Figure 1:
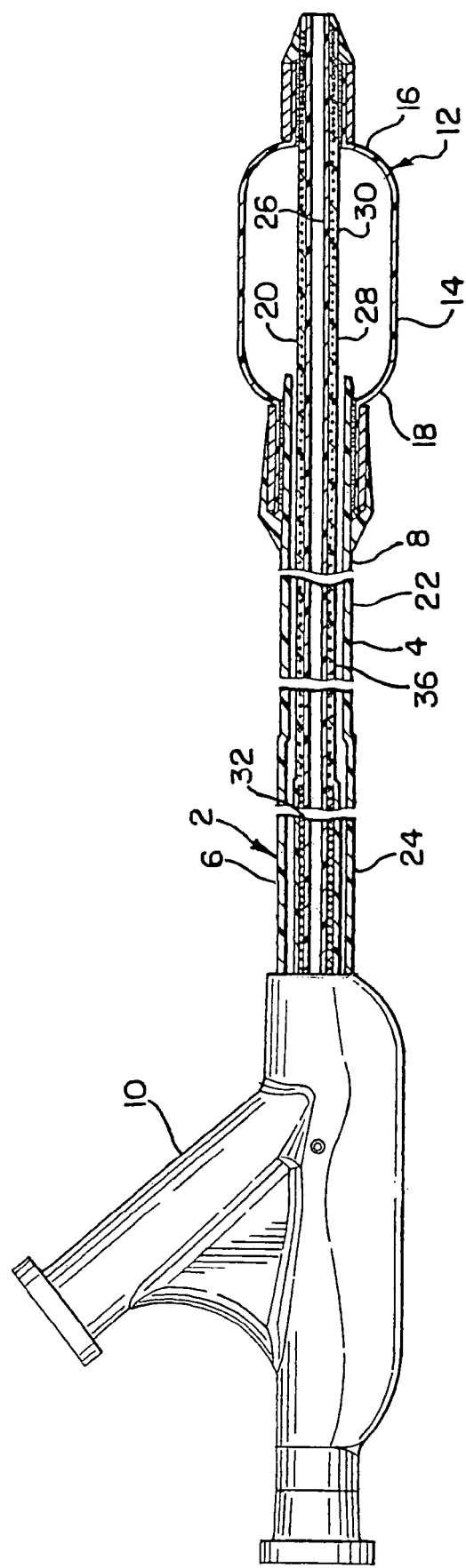
FIG. 1 is a longitudinal cross-sectional view illustrating a balloon catheter made in accordance with the invention.

FIG. 1 illustrates a simplified cross-sectional view of a balloon catheter made in accordance with the present invention. The balloon catheter 2 includes an outer tubular member 4 having a proximal end 6 and a distal end 8. A dual port Y-connector 10 is coupled to the proximal end 6 of the outer tubular member 4. An inflatable balloon 12 having a main body portion 14 and proximal and distal portions 18, 16, respectively, is secured to the distal end of the outer tubular member 4 at the proximal portion 18 of the inflatable balloon 12. The distal portion 16 of the inflatable balloon 12 is, in turn, secured to the distal end of an inner tubular member 20.

As illustrated, the outer tubular member 4 includes a distal portion 22 and a proximal portion 24 of differing diameters. The proximal portion 24 is formed from nylon having a durometer of 75D, and the distal portion 22 is formed of polyurethane having a durometer of 65D. In addition, the outside diameter of the proximal portion 24 of the outer tubular member is approximately 0.043 inches, the inside diameter of this proximal portion is 0.038 inches with the result that the wall thickness of the proximal portion of the outer tubular member is about 0.0025 inches. The distal portion 22 of the outer tubular member has an outer diameter of 0.0365 inches, an inside diameter of 0.0315 inches with the result that the wall thickness of the distal portion of the outer tubular member is about 0.0025 inches. With the resulting reduction in diameter of the proximal portion of the outer tubular member 4, the distal section of the catheter becomes more flexible and therefore may be more easily passed through the tortuous vessels of the human body.

The inner tubular member 20 is comprised of a thin inner layer 26, a reinforcing layer 28 placed on top of the inner layer 26 and a soft outer layer 30 which surrounds and bounds the reinforcing layer 28 to the inner layer 26. The reinforcing layer 28 is comprised of a proximal reinforcing layer 32 which is formed from braided stainless steel wires and a distal reinforcing layer 36 which is formed from a single helically wound platinum wire. The soft outer layer 30 is heat bonded onto the reinforcing layer 28. Accordingly, with the proximal section of the catheter having an inner tubular member formed with a braided reinforcing layer, this section of the catheter becomes relatively stiff and has a relatively high column strength so that the catheter may be pushed into and through the vasculature of the human body. On the other hand, the distal section of the catheter is formed with an inner tubular member which is comprised of a single helically wound wire which, while being sufficiently stiff to resist kinking, is still very flexible and is capable of traversing tortuous vessels.

As may now be appreciated, with the balloon catheter as illustrated in FIG. 1, the proximal section of the catheter is formed with an outer tubular member portion of an increased diameter and an inner tubular member which is formed by bonding a reinforcing layer of woven stainless steel wires between two polymer layers thereby providing a proximal catheter section which exhibits the characteristic of having relatively high column strength. The distal section of the catheter is formed with an outer tubular member having a reduced outer and inner diameter and with a single helically wound wire bonded between two polymer tubular members to thereby provide a distal section which is relatively kink resistant, but still remains very flexible.

Figure 2:
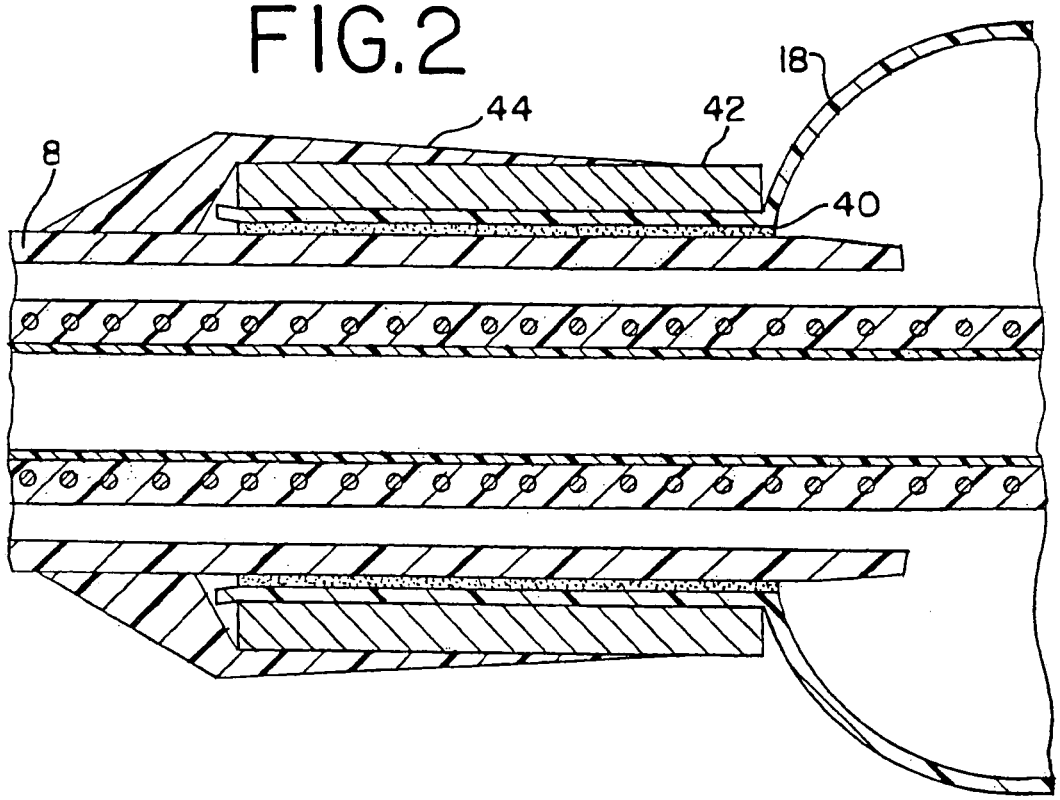
FIG. 2 is a longitudinal cross-sectional view illustrating the improved attachment structure for the proximal balloon junction; and, FIG. 3 is a, longitudinal cross-sectional view illustrating the improved attachment structure for the distal balloon junction.

FIG. 2 illustrates the seal at the proximal end 18 of the balloon and is accomplished as follows. The distal end 8 of the outer tubular member is tapered by applying a heat shrinkable tube over the distal end 8 of the outer tubular member and heat fusing over a mandrel. The heat shrinkable tube and mandrel are then removed. The first layer of adhesive material 40 is applied to the tapered section of the outer tubular member 4. The proximal portion 18 of the balloon 12 is inserted over the adhesive-covered tapered section of the distal end 8 of the outer tubular member 4, such that the inner surface of the proximal portion 18 of the balloon is in contact with the first layer of adhesive material 40. A first retaining ring 42 is positioned over the proximal end 18 of the balloon 12 and is crimped onto the proximal end 18 of the balloon 12 by some mechanical means, such as a crimping fixture. Finally, the proximal marker band sleeve 44 is positioned over at least a half of the proximal end of the first retaining ring 42. The assembly is covered with a seal sleeve made of heat shrink material and heat is applied allowing the seal sleeve to conform to the underlying assembly and heat fusing the proximal marker band sleeve 44 to the outer tubular member 4 and the first retaining ring 42. The seal sleeve is then removed from the assembly after it has cooled.

Figure 3:
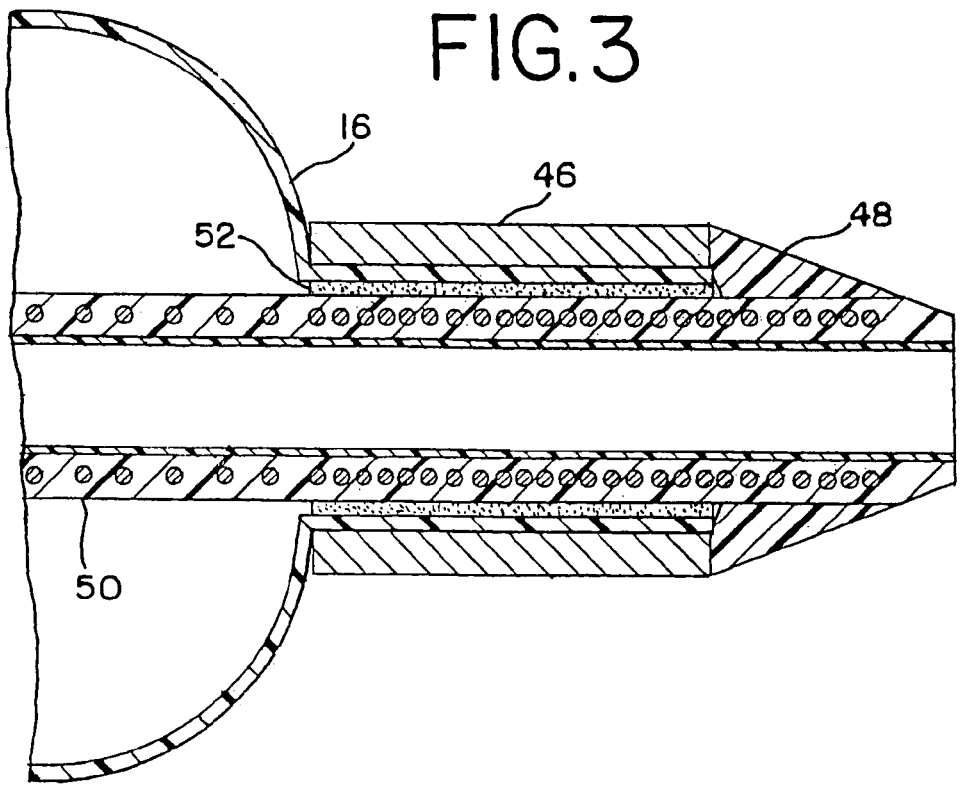

FIG. 3 illustrates the seal at the distal portion 16 of the balloon and is accomplished as follows. First, the distal end 50 of the inner tubular member 20 is inserted inside the distal portion 16 of the balloon. A second retaining ring 46 is positioned over the distal portion 16 of the balloon 12 and the distal end 50 of the inner tubular member 20. A second layer of adhesive material 52 is applied onto the distal end 50 of the inner tubular member 20 and under the distal portion 16 of the balloon 12, such that the inner surface of the distal portion 16 of the balloon is in contact with the second layer of adhesive material 52. The second retaining ring 46 is crimped onto the distal end 16 of the balloon 12 by some mechanical means, such as a crimping fixture, and excess balloon material is trimmed distal to the second retaining ring 46. The distal marker band sleeve 48 is inserted over the distal end 50 of the inner tubular member 20. The assembly is covered with a heat shrink tube and heat is applied, allowing the heat shrink tube to conform to the underlying assembly and heat fusing the distal marker band sleeve 48 to the inner tubular member 20 distal to the second retaining ring 46. Once the assembly has cooled, the heat shrink tube is removed.

The first and second retaining rings, 42 and 46, respectively, are made of a radiopaque and biocompatible material, preferably gold, allowing for the precise positioning of the inflatable balloon as it is deployed into the human body. The marker band sleeves provide support for the retaining rings and prevent them from moving along the length of the outer or inner tubular members, especially when the balloon is inflated. Additionally, the marker band sleeves help to ensure that the retaining rings do not become separated from the assembly in the event that the balloon ruptures.

In a preferred construction of the present invention, the outer tubular member 4 is formed from polyurethane material and the inflatable balloon 12 is formed from silicone material. The outside diameter of the proximal section of the outer tubular member 4 has an outside diameter of 0.043 inches and an inside diameter of 0.038 inches. The distal section of the outer tubular member 4 has an outside diameter of 0.0365 inches and an inside diameter of 0.0315 inches. In addition, the thin inner layer 26 of the inner tube member 20 is formed from PTFE material and has a thickness of approximately 0.0015 inches. The soft outer layer 30 of the inner tubular member 20 is preferably formed of polyurethane material and has a thickness of approximately 0.0025 inches.

The helical wound coil in the distal reinforcing layer 34 is formed of platinum wire having a circular cross section and with a diameter of approximately 0.0015 inches, and the braiding in the proximal reinforcing layer 32 is formed of stainless steel wire of circular cross-section. The wire forming the stainless steel braid preferably has a diameter of about 0.0015 inches.

The layers of adhesive material are formed from silicone approximately 0.001 inches thick. The length of the first layer is 0.040 inches and the length of the second layer is 0.023 inches. The first retaining ring 42 has a nominal diameter of 0.0375 inches and decreases by approximately 0.002 inches after being crimped. The first retaining ring 42 is approximately 0.040 inches wide. The second retaining ring 46 has a nominal diameter of 0.030 inches and decreases by approximately 0.0025 inches after being crimped. The second retaining ring 46 is approximately 0.023 inches wide.

The first marker band sleeve is made from nylon material with an outer diameter of 0.0385 inches, an inner diameter of 0.036 inches, and a length of 0.040 inches. The first marker band sleeve is positioned such that it overlaps at least half of the length of the first retaining ring. The second marker band sleeve is made from polyurethane material with an outer diameter of 0.0315 inches, an inner diameter of 0.0275 inches, and a length of 0.030 inches. The materials for the marker band sleeves were chosen relative to the durometers of the outer and inner tubular members that the marker band sleeves are attached to. The inner tubular member is more flexible than the outer tubular member is, so a more flexible material was chosen for the second marker band sleeve.

With the balloon catheter of the present invention, fluid may be applied through a lumen in the side port of the Y-connector 10 which communicates with the passageway between the inner tubular member 20 and the outer tubular member 4 to thereby inflate the balloon 12. In order to steer the catheter through the vasculature, a guidewire is typically passed through the proximal port of the Y-connector 10 and through the inner lumen of the inner tubular member which serves to assist in steering the distal tip of the catheter through the vasculature.

As is apparent, there are numerous modifications of the preferred embodiment described above that will be readily apparent to one skilled in the art to which this invention relates. These modifications are intended to be within the scope of the claims that follow.

That which is claimed is:

1. A method of manufacturing a balloon catheter which includes an outer tubular member having proximal and distal ends; an inner tubular member having proximal and distal ends, said inner tubular member being coaxial with said outer tubular member, said inner tubular member running longitudinally through said outer tubular member and extending distally beyond the distal end of said outer tubular member; an inflatable balloon having a main body portion and proximal and distal portions extending from said main body portion, said proximal and distal portions each having an inner and outer surface and a retaining ring crimped over the outer surface; and a proximal retaining sleeve at the balloon proximal end portion; wherein the method comprises the steps of:

applying a first layer of adhesive material to the distal end of the outer tubular member;

inserting the proximal portion of the balloon over the section of the outer tubular member covered by the first layer of adhesive material such that the balloon and the outer tubular member are coaxially oriented;

positioning a first retaining ring over the proximal portion of the balloon;

crimping a first retaining ring onto the proximal portion of the balloon;

inserting the inner tubular member inside the balloon;

positioning a second retaining ring over the balloon;

applying a second layer of adhesive material onto the distal end of the inner tubular member at a location beneath the distal potion of the balloon;

crimping the second retaining ring onto the distal portion of the balloon;

positioning a proximal retaining sleeve to overlap at least a portion of the crimped first retaining ring and a section of the outer tubular member that is immediately proximally adjacent to the crimped first retaining ring; and heat fusing the proximal retaining sleeve to the crimped first retaining ring and to the outer tubular member section while conforming the proximal retaining sleeve to enclose the proximal portion of the first retaining ring thereby preventing the first retaining ring from moving along the length of the outer tubular member.

2. A method of manufacturing a balloon catheter as described in claim 1, wherein at least a portion of the distal end of the outer tubular member is tapered prior to applying the first layer of adhesive material over the portion of the distal end which is tapered.

3. A method of manufacturing a balloon catheter as described in claim 1, further including positioning a distal retaining sleeve distally adjacent to the crimped second retaining ring; and heat fusing the distal retaining sleeve to the inner tubular member at a section thereof immediately distally adjacent to the crimped second retaining ring thereby preventing the second retaining ring from moving along the length of the inner tubular member.

4. A method of manufacturing a balloon catheter as described in claim 1, wherein said heat fusing includes placing a heat shrinkable sleeve over the proximal retaining sleeve and applying heat thereto.

5. A method of manufacturing a balloon catheter as described in claim 3, wherein said heat fusing of the distal retaining sleeve includes placing a heat shrinkable sleeve over the distal retaining sleeve and applying heat thereto.

6. A method of manufacturing a balloon catheter as described in claim 1, further including forming the first retaining ring of a radiopaque material.

7. A method of manufacturing a balloon catheter as described in claim 3, further including forming the second retaining ring of a radiopaque material.

8. A method of manufacturing a balloon catheter as described in claim 1, wherein said heat fusing includes overlapping the proximal portion of the first retaining ring by at least half of the length thereof.

* * * * *